(12) United States Patent
Savant

(10) Patent No.: US 11,690,611 B2
(45) Date of Patent: Jul. 4, 2023

(54) SUTURING DEVICES FOR LAPAROSCOPIC SURGERY

(71) Applicant: Gaurav Savant, Shrewsbury, MA (US)

(72) Inventor: Gaurav Savant, Shrewsbury, MA (US)

(*) Notice: Subject to any disclaimer, the term of this patent is extended or adjusted under 35 U.S.C. 154(b) by 204 days.

(21) Appl. No.: 17/209,945

(22) Filed: Mar. 23, 2021

(65) Prior Publication Data

US 2022/0304675 A1 Sep. 29, 2022

(51) Int. Cl.
*A61B 17/04* (2006.01)
*A61B 17/06* (2006.01)
*A61B 17/00* (2006.01)

(52) U.S. Cl.
CPC ...... *A61B 17/0469* (2013.01); *A61B 17/0493* (2013.01); *A61B 17/06066* (2013.01); *A61B 2017/00398* (2013.01); *A61B 2217/005* (2013.01)

(58) Field of Classification Search
CPC . A61B 17/04; A61B 17/0469; A61B 17/0482; A61B 17/0493; A61B 17/06066; A61B 17/0625; A61B 2017/00398; A61B 2217/005
See application file for complete search history.

(56) References Cited

U.S. PATENT DOCUMENTS

| | | | | |
|---|---|---|---|---|
| 5,306,281 A | * | 4/1994 | Beurrier | A61B 17/0491 112/80.03 |
| 5,891,159 A | * | 4/1999 | Sherman | A61B 17/0482 606/139 |
| 6,461,366 B1 | * | 10/2002 | Seguin | A61B 17/068 606/139 |
| 2006/0287657 A1 | * | 12/2006 | Bachman | A61B 17/0401 606/139 |
| 2019/0374220 A1 | * | 12/2019 | Fischell | A61B 17/0482 |

OTHER PUBLICATIONS apolloendo.com, "Welcome to Apollo Endosurgery," retrieved Oct. 6, 2021 from URL <https://apolloendo.com>, 3 pages.
Kelly et al., "Proxisure Suturing System," Dec. 11, 2017, retrieved Oct. 6, 2021 from URL <https://www.sages.org/publications/tavac/proxisure-suturing-system>, 3 pages.
overstitch.com, "Overstitch Endoscopic Suturing System," retrieved Oct. 6, 2021 from URL <https://www.overstitch.com/overstitch-sx>, 6 pages.

(Continued)

*Primary Examiner* — Tuan V Nguyen
(74) *Attorney, Agent, or Firm* — Fish & Richardson P.C.

(57) ABSTRACT

Some suturing devices include a pair of flexible arms configured to force two pieces of tissue together and form a protrusion defined by the two pieces of tissue. Some suturing devices include a third flexible arm including a movable needle configured to apply a suture through both pieces of tissue of the protrusion. Some suturing devices include an actuator configured to move each flexible arm of the pair of flexible arms independently relative to the tissue and move the third flexible arm relative to the tissue. Some suturing devices include a pump configured to generate a suction force through the pair of flexible arms to force the tissue towards the pair of flexible arms.

15 Claims, 12 Drawing Sheets

(56) References Cited

OTHER PUBLICATIONS sages.org. "Society of American Gastrointestinal and Endoscopic Surgeons," retrieved Oct. 6, 2021 from URL <https://www.sages.org/>, 6 pages.

youtube.com. Drone Bot Workshop, "Stepper Motors with Arduino—Controlling Bipolar & Unipolar stepper motors," Feb. 10, 2018, retrieved Oct. 6, 2021 from URL <https://www.youtube.com/watch?v=0qwmUeSpYQ>, 1 page.

* cited by examiner

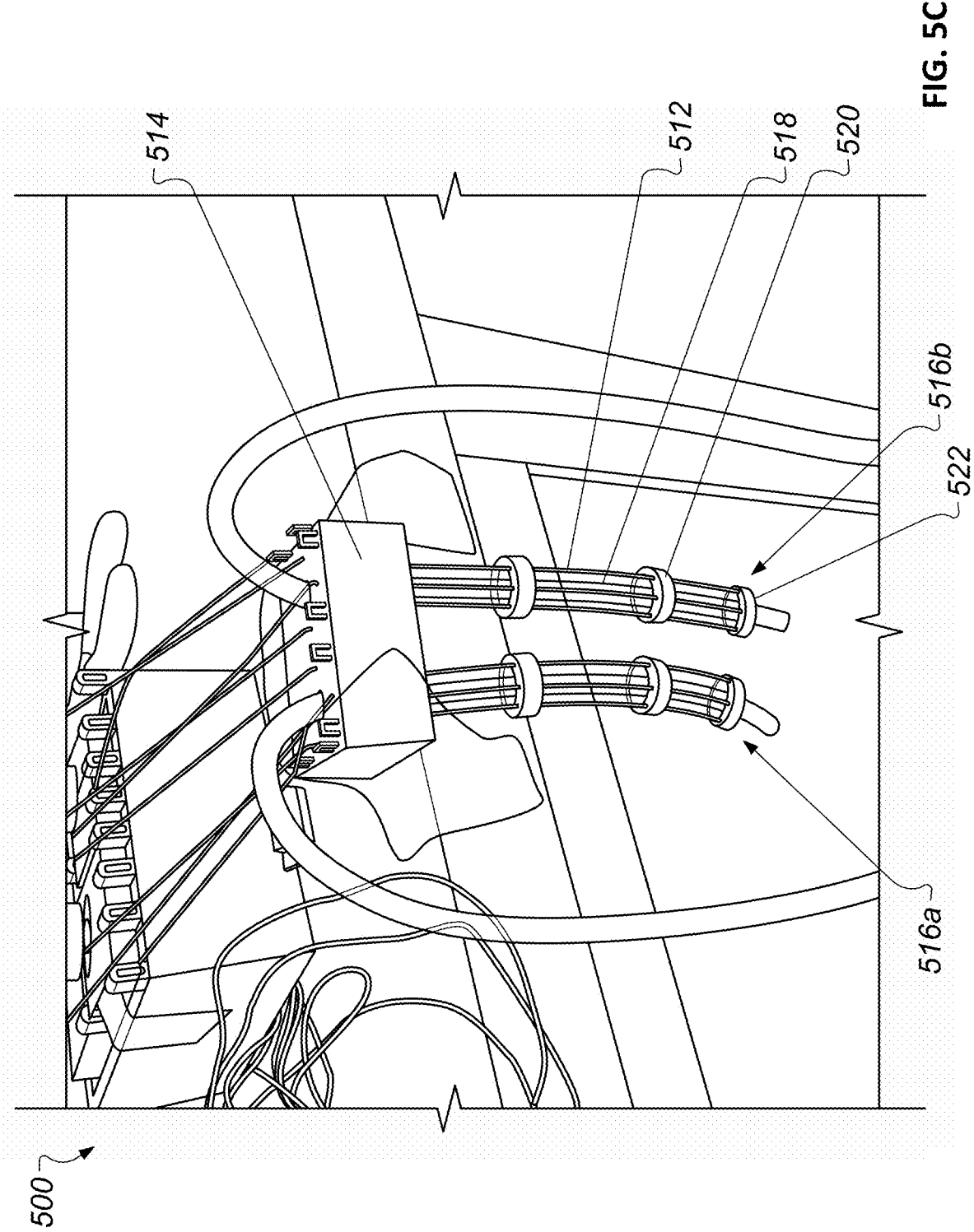

SUTURING DEVICES FOR LAPAROSCOPIC SURGERY

BACKGROUND

1. Technical Field

This document relates to suturing devices for laparoscopic surgery.

2. Background Information

Applying sutures can be a difficult process. Typical suturing devices only suture a single tissue at a time which requires a surgeon to physically move the suturing device to a second tissue to suture the two tissues together. This makes it difficult to apply sutures between disconnected tissues. These devices also have difficulty when suturing large incisions because of this required physical movement.

Another technique is to use a hand suturing technique where the surgeon controls a tool to physically weave a needle through respective tissues to apply a suture. These techniques require high precision and can leave a patient more susceptible to complications such as hemorrhaging if the technique is not performed properly.

SUMMARY

This document describes suturing devices for laparoscopic surgery. The suturing devices are controllable by a surgeon to apply sutures to incisions. The suturing devices include flexible arms to manipulate tissue using suction and a force squeezing the tissue between the flexible arms. Once the tissue is held in place, the suturing device applies a suture through both pieces of the tissue using a movable needle. Importantly, the suture is applied to both pieces of tissue without having to reorient the movable needle.

Laparoscopic surgery is a minimally invasive surgical procedure that involves making small incisions (e.g., generally 0.5 to 1 cm wide incisions) in an abdomen or pelvis area of a patient. Laparoscopic surgery is often used to perform surgery on organs (e.g., stomach, gallbladder, colon, kidney, etc.) and to inspect female reproduction organs (e.g., uterus, ovaries, fallopian tubes, etc.). During laparoscopic surgery, a surgeon makes incisions in the abdominal wall as well as in these organs and then must apply a suture to these incisions. In this way, the suturing device described herein can be used for suturing incisions on the surface of the patient as well as for suturing internal incisions of the patient's organs. Generally, sutures are stitches or rows of stitches that hold two pieces of tissue of the organ together.

In a first aspect, a suturing device includes a pair of flexible arms configured to force two pieces of tissue together and form a protrusion defined by the two pieces of tissue. The suturing device includes a third flexible arm including a movable needle configured to apply a suture through both pieces of tissue of the protrusion. The suturing device includes an actuator configured to move each flexible arm of the pair of flexible arms independently relative to the tissue and move the third flexible arm relative to the tissue. The suturing device includes a pump configured to generate a suction force through the pair of flexible arms to draw the tissue towards the pair of flexible arms.

The suturing device may optionally include one or more of the following features.

In some implementations, each flexible arm of the pair of flexible arms includes a hollow tube configured to engage the tissue. In some cases, the pump is configured to generate the suction force through each hollow tube. In some cases, each hollow tube includes cables within the sidewall of the hollow tube. In some cases, the cables are movable along a longitudinal axis of the hollow tube and movable with respect to the sidewall of the hollow tube.

In some implementations, the actuator includes a plurality of motors with winding modules.

In some implementations, the suturing device includes a needle motor configured to cause the movable needle to rotate about an axis perpendicular to a longitudinal axis of the third flexible arm.

In some implementations, the movable needle is a semi-circular needle movable relative to the third flexible arm.

In some implementations, the tissue is a tissue of an anatomical organ.

In some implementations, the pump is a vacuum pump.

In some implementations, the actuator includes a plurality of stepper motors.

In some implementations, at least a portion of the pair of flexible arms and the at least a portion of the third flexible arm are disposed inside an endoscope In some implementations, the suturing device includes a processor configured to control movement of the pair of flexible arms, the third flexible arm, and an angular position of the movable needle with respect to the third flexible arm. In some cases, the processor is controllable by an input device.

In some implementations, a distal end of each flexible arm comprises a flange that engages the tissue.

In a second aspect, a computer-implemented method for using a suturing device includes orienting, by a processor, a pair of flexible arms relative to two pieces of tissue. The computer-implemented method includes forcing the two pieces of tissue together to form a protrusion using each flexible arm of the pair of flexible arms. The computer-implemented method includes orienting, by the processor, a third flexible arm relative to the two pieces of tissue. The computer-implemented method includes moving a needle relative to the third flexible arm to apply a suture through both pieces of tissue forming the protrusion.

The computer-implemented method of using the suturing device may optionally include one or more of the following features.

In some implementations, the computer-implemented method includes pumping, by the processor, air to cause a suction between the tissue and each flexible arm of the pair of flexible arms, wherein the suction is used to draw the two pieces of tissue toward the corresponding flexible arm, and the flexible arms are moved together to form the protrusion.

In some implementations, orienting the pair of flexible arms relative to two pieces of tissue includes moving cables of each flexible arm of the pair of flexible arms using a plurality of motors.

In some implementations, moving the needle relative to the third flexible arm to apply the suture through both pieces of tissue includes controlling an angular orientation of the needle.

In some implementations, the computer-implemented method includes moving the third flexible arm along the protrusion and applying a suture at a plurality of locations along the protrusion.

Particular embodiments of the subject matter described in this document can be implemented to realize one or more of the following advantages.

A suturing device with a suction capability can force the tissue to engage with the flexible arms to allow better manipulation of the tissue compared to a suturing device without a suction capability. Some suturing devices use a pump with a pneumatic variable pressure so the surgeon can change the suction pressure during the suturing procedure.

Traditional suturing devices are oriented to a first tissue, apply a first suture to the first tissue, then move to a second tissue, suture the second tissue, then pull a thread tightly to force the two pieces of tissue tougher. A suturing device that can apply a suture through two pieces of tissue without having to be reoriented is advantageous because it requires less movement of the suturing device.

A suturing device as described herein can be used for internal incisions (e.g., organ incision) as well as incisions on a surface of the patient (e.g., skin incisions). This means the suturing device is useable in multiple scenarios without the surgeon needing to change the suturing device.

A suturing device that can fit within an endoscope is advantageous because it can be used during laparoscopic surgery.

The details of one or more implementations of the invention are set forth in the accompanying drawings and the description herein. Other features, objects, and advantages of the invention will be apparent from the description and drawings, and from the claims.

DESCRIPTION OF THE DRAWINGS

FIGS. 5A-5E illustrate an example suturing device.

Like reference numbers represent corresponding parts throughout.

DETAILED DESCRIPTION

This document describes suturing devices for laparoscopic surgery. The suturing devices are controllable by a surgeon to apply sutures to incisions. The suturing devices include flexible arms to manipulate tissue using suction and a force squeezing the tissue between the flexible arms. Once the tissue is held in place, the suturing device applies a suture through both pieces of the tissue using a movable needle. The suture is applied to both pieces of tissue without having to reorient the suture needle.

Figure 1:
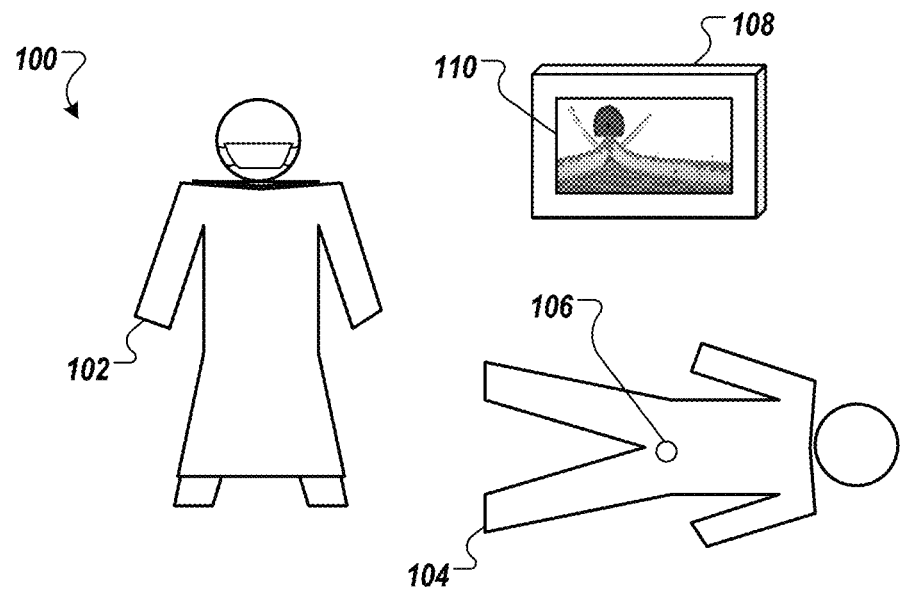
FIG. 1 illustrates a surgical environment for performing laparoscopic surgery.

FIG. 1 shows a surgeon 102 performing a laparoscopic surgical procedure on a patient 104 within a surgical environment 100. The surgeon makes one or more topical incisions 106 in the patient 104. In this example, the surgeon is performing a laparoscopic surgical procedure and the topical incisions 106 are in the patient's abdominal area. The surgeon 102 inserts an endoscope (or laparoscope, trochar, etc.) through the topical incisions 106 to perform the surgery as needed. For example, the surgeon 102 can insert a laparoscope with a camera into the topical incisions 106 to view the abdominal organs. In this example, the surgeon views the organs on an external monitor 108 that shows images 110 from the camera.

Figure 2:
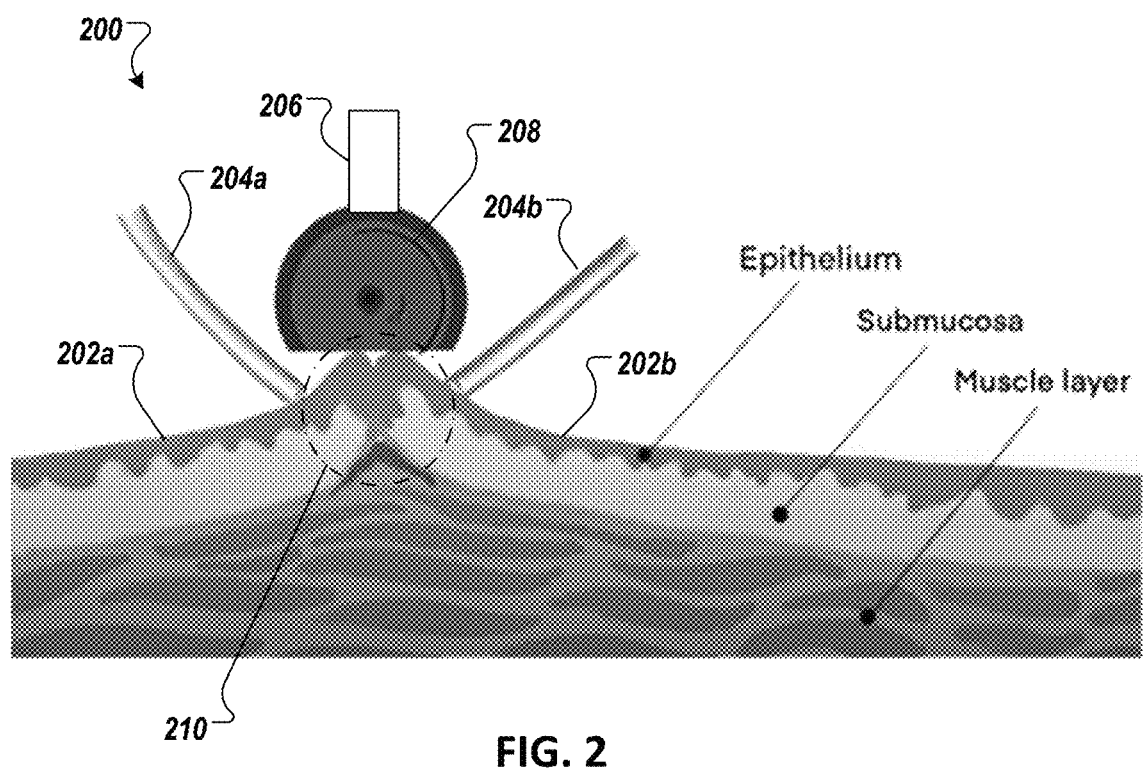
FIG. 2 illustrates a suturing device applying a suture to two pieces of tissue.

FIG. 2 shows a suturing device 200 suturing two tissues 202a, 202b (generally 202) together. In this example, the tissue 202 includes a layer of epithelium, submucosa, and a muscle layer. Typically, the suture is applied through the epithelium and the submucosa layers.

The suturing device 200 includes a pair of flexible arms 204a, 204b (generally 204) and a movable needle 208 that is attached to a third flexible arm 206. The pair of flexible arms and the third flexible arm 206 are independently movable using an actuator (not explicitly shown in FIG. 2). The movable needle 208 is also independently movable to apply a suture.

Figure 3:
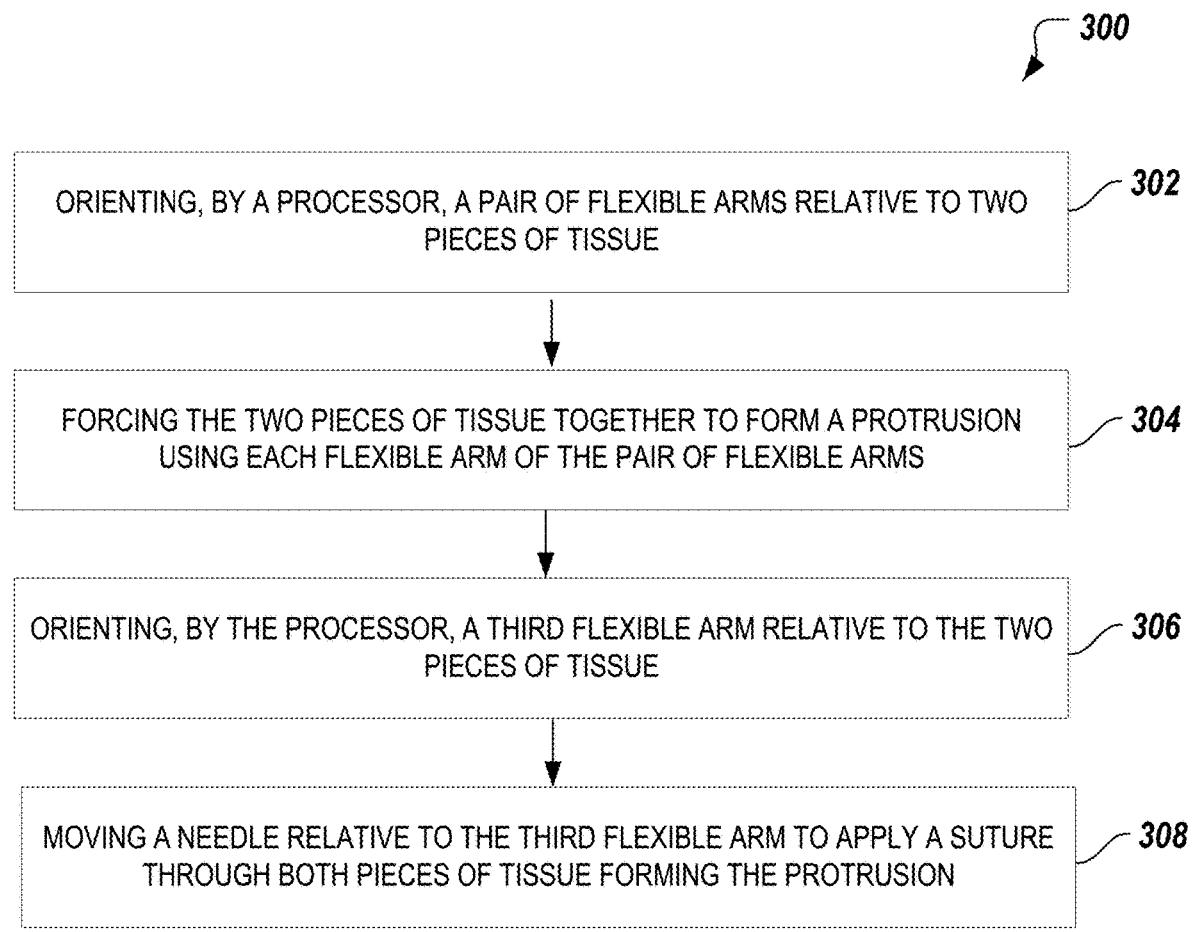
FIG. 3 is a flowchart of a computer-implemented method of using a suturing device.

FIG. 3 is a flowchart of a computer-implemented method of using a suturing device according to some embodiments. In some examples, the computer-implemented method is implemented by a computing device 700 and/or a mobile computing device 750 described with reference to FIG. 7 below. The method includes, at step 302, orienting, by a processor, a pair of flexible arms relative to two pieces of tissue. For example, an actuator, controlled by the processor, orients the pair of flexible arms 204 relative to the two pieces of tissue 202 as shown in FIG. 2.

The method includes, at step 304, forcing the two pieces of tissue together to form a protrusion using each flexible arm of the pair of flexible arms. For example, an actuator moves the pair of flexible arms 204 to engage the tissue 202 and, by forcing the flexible arms 204 together, the two pieces of tissue 202 are forced together to form a protrusion 210.

The method includes, at step 306, orienting, by the processor, a third flexible arm relative to the two pieces of tissue. For example, the actuator, controlled by the processor, orients the third flexible arm 206 relative to the two pieces of tissue 202 in anticipation of applying a suture.

The method includes, at step 308, moving a needle relative to the third flexible arm to apply a suture through both pieces of tissue forming the protrusion. For example, the actuator, controlled by the processor, moves the movable needle 208 relative to the third flexible arm 206 to apply a suture through both pieces of tissue forming the protrusion 210. In some examples, the actuator controls an angular orientation of the movable needle 208 to apply the suture. For example, the movable needle rotates about an axis perpendicular to a longitudinal axis of the third flexible arm and the rotation about this axis is the angular position of the movable needle 208. In some embodiments, a needle motor causes the rotational movement of the movable needle 208.

Figure 4A:
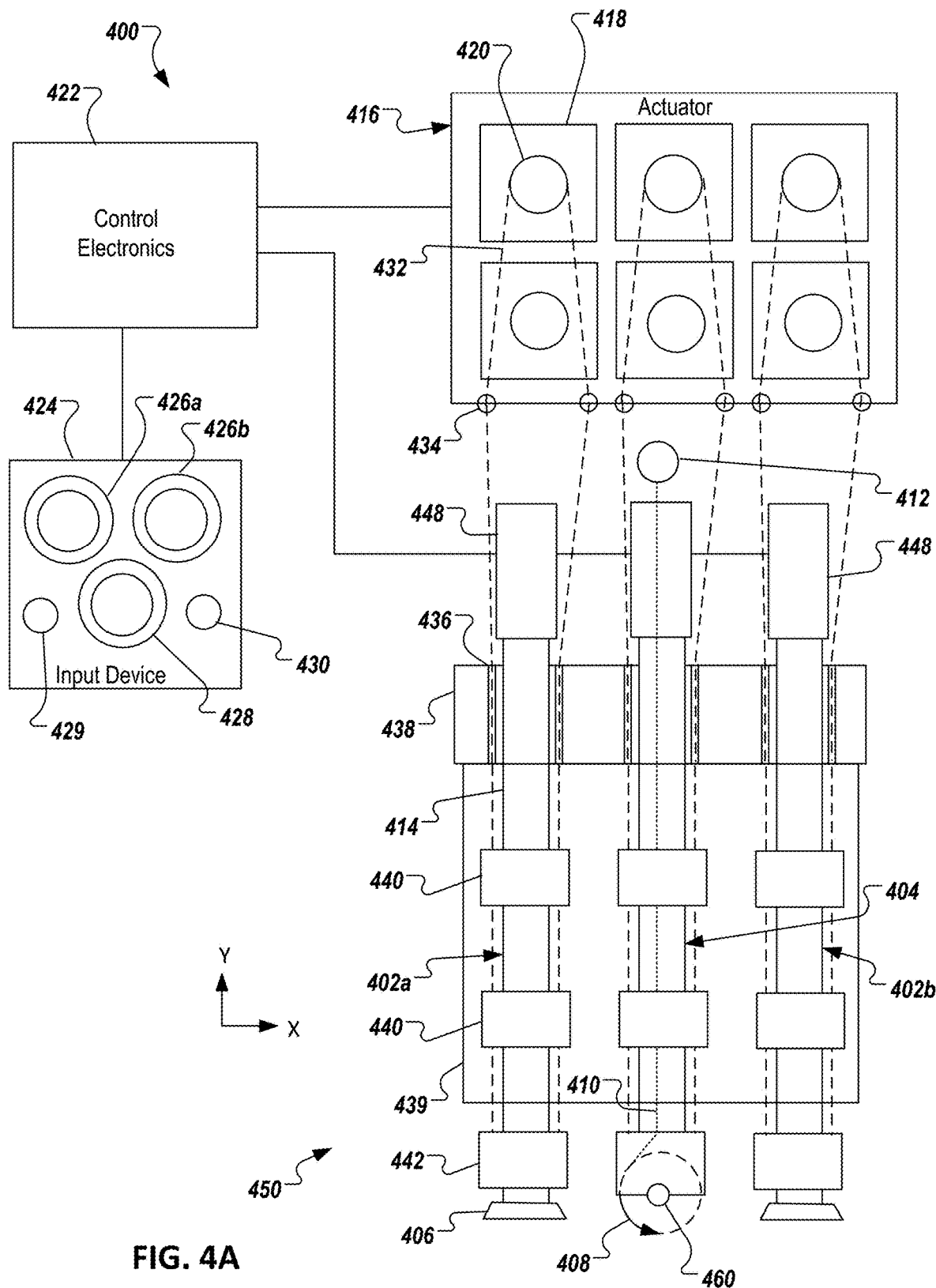
FIGS. 4A-4D are schematics of a suturing device with three flexible arms and example uses of the suturing device to apply a suture to two pieces of tissue.
Figure 4B:
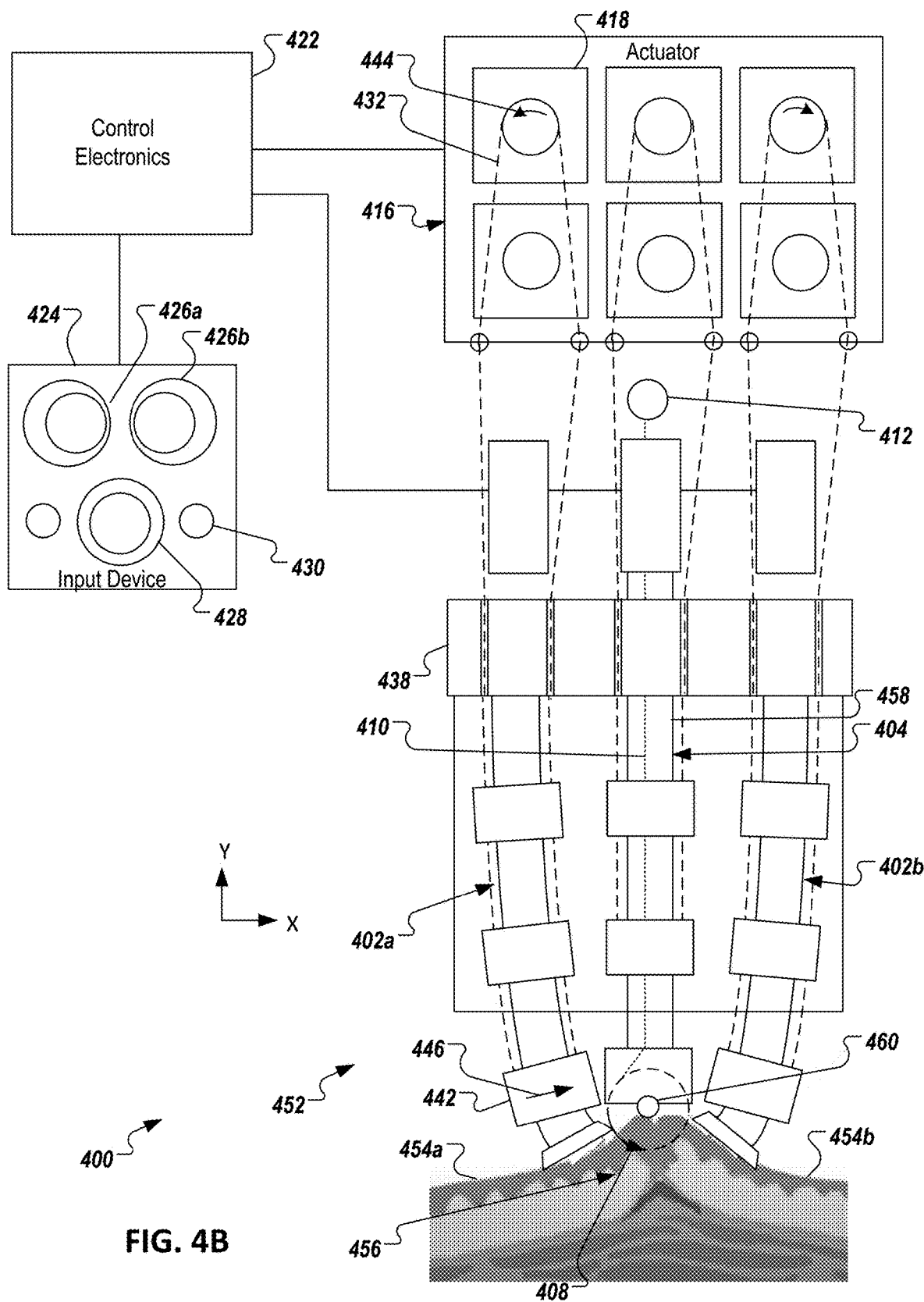

FIGS. 4A and 4B are schematics of a suturing device 400 with three flexible arms in a straight configuration and a flexed configuration, respectively. In some embodiments, the suturing device 400 is substantially similar to, or the same as, the suturing device 200 described with reference to FIG. 2 above. The suturing device 400 includes a pair of flexible arms 402a, 402b (generally 402) for manipulating tissue and a third flexible arm 404 for applying the suture to the tissue. Each of the flexible arms 402 includes a flange 406 at its distal end to engage with the tissue and distribute the contact pressure to the tissue. In the example shown, the flange 406 is a trapezoidal shape. In other examples, the flange 406 is a semi-spherical shape.

The third flexible arm 404 includes a movable needle 408 that rotate about an axis perpendicular to a longitudinal axis of the third flexible arm 404. The movable needle 408 is a semi-circular shape and movable relative to the third flexible arm 404. In some examples, a needle motor 460 causes the rotational movement of the movable needle 408. The movable needle 408 is connected to a sterile thread 410 that is used to hold the two pieces of tissue together after the suture is applied. The suturing device 400 includes a thread supply 412 of the sterile thread 410. The sterile thread 410 and how the sterile thread 410 is used to hold the tissue together is further described with reference to FIG. 4D below.

Each flexible arm 402a, 402b of the pair of flexible arms 402 includes a hollow tube 414. In some examples, the hollow tube 414 includes vinyl tubing with a 0.25 inch outside diameter, but other diameters can be used (e.g., 0.5 inch, 0.75 inch, etc.) The hollow tube 414 is structurally compliant to allow the entire flexible arm 402 to flex by hand and/or by actuation forces of an actuator 416. For example, the actuator 416 actuates the flexible arms 402 to flex between a straight configuration 450, where the flexible arms 402 are substantially straight, and a flexed configuration 452 (shown in FIG. 4B) where the flexible arms 402 are flexed.

The actuator 416 includes a plurality of stepper motors 418 (e.g., NEMA-14 stepper motors) that are controlled by control electronics 422. The control electronics 422 include one or more processors for implementing the computer-implemented method of the suturing device 400. In some examples, the control electronics 422 includes a computing device 700 and/or a mobile computing device 750 described with reference to FIG. 7 below.

The control electronics 422 are connected to an input device 424 and are controllable by the input device 424. For example, the input device 424 includes a pair of joysticks 426a, 426b (generally 426). Each joystick 426 is maneuverable (e.g., by the surgeon) to control the orientation of one of the flexible arms 402. In this way, both joysticks 426 allow the surgeon to control each flexible arm 402a, 402b of the pair of flexible arms 402 to allow the surgeon to manipulate the tissue and form a protrusion for applying the suture. A third joystick 428 is maneuverable to control the orientation of the third flexible arm 404. In this way, the joystick 428 allows the surgeon to control the flexible arm to orient the third flexible arm 404 for applying the suture through the protrusion.

The input device 424 includes buttons 429, 430 for controlling a suction force for engaging the tissue and an angular position of the movable needle 408 with respect to the third flexible arm 404, respectively. For example, the surgeon presses the button 430 to cause the movable needle 408 to rotate and releases the button 430 to cause the movable needle 408 to stop rotating (e.g., by the action of the needle motor 460). In some examples, each press of the button 430 advances the movable needle 408 a predetermined length of the complete circular path of the movable needle 408 (e.g., $\frac{1}{10}^{th}$ of a rotation, etc.) Aspects related to the suction force are described below after the components to produce the suction force are introduced.

Referring back to the actuator 416, each stepper motor 418 includes a winding module 420 that maintains two spools of a cable 432. In this way, the actuator 416 includes a plurality of motors 418 with winding modules 420. The two spools are oppositely wound so a rotation in a first direction unwinds one cable spool while winding the other cable spool, and vice versa. The spools are further described with reference to FIG. 5B below. The cable 432 passes through openings 434 of the actuator and the cable 432 passes through openings 436 in an end cap 438. The end cap 438 is a mount for all of the flexible arms 402, 404. In this way, at least a portion of the pair of flexible arms 402 and at least a portion of the third flexible arm 404 are disposed inside an endoscope 439 that can be used during a laparoscopic surgical procedure. For example, at least a portion of the pair of flexible arms 402 and at least a portion of the third flexible arm 404 are disposed inside a 15 mm diameter tube of the endoscope 439. In such examples, the end cap 438 can be attached to a proximal end of the endoscope 439. During use, such an endoscope 439 could be hand-held by the surgeon and/or held in place using a support structure (not shown). For example, a support structure can be a movable arm that the surgeon can maneuver above the suturing site of the patient. In either case, the surgeon can position the endoscope 439 such that the flexible arms 402 protrude from a distal end of the endoscope 439 to apply a suture. For example, the details of applying sutures are described below with reference to FIG. 4D.

The cable 432 passes through two aligner blocks 440 and terminates at an end block 442. Importantly, each flexible arm 402 includes at least two cables 432 so the control electronics 422 can control the orientation of the flexible arm 402. For example, the flexible arm 402 is controllable about a pendulum-like path. One cable 432 is used to pull the flexible arm 402 to one side of the pendulum path, while another cable 432 is used to pull the flexible arm 402 to the other side of the pendulum path.

In some examples, the cables 432 on each side of the flexible arm 402 is tied to the end block 442. The cables 432 freely slide through the aligner blocks 440, the end cap 438 and the openings 434 of the actuator 416. For example, with reference to FIG. 4B, when the winding module 420 spins in a first direction (denoted by arrow 444), the cable 432 on the right-hand side (e.g., as viewed in the plane of FIG. 4B) of the spool winds onto the spool. This causes the cable 432 to become taught and pulls the end block 442 toward the end cap 438. In turn, this causes the distal end of the flexible arm 402a to move to the right-hand side (denoted by arrow 446). Simultaneously, the cable 432 on the left-hand side of the spool unwinds from the spool. This causes the cable 432 to become loose and allows the end block 442 to move under the force of the other thread to allow the movement denoted by arrow 446.

Similarly, the other flexible arm 402b has substantially the same configuration such that the distal ends of both flexible arms 402 can move toward each other under the action of the actuator 416. For example, when a surgeon manipulates the joysticks 426 of the input device 424 toward each other (e.g., as shown in the illustration of FIG. 4B), the processor of the control electronics 422 sends a control signal to the stepper motors 418 of the actuator 416. The control signal instructs the stepper motors 418 to simultaneously wind and unwind cable 432 to cause each of the flexible arms 402 to move in a direction corresponding to a direction of the joysticks 426. In this way, the processor of the control electronics 422 is configured to control movement of the pair of flexible arms 402. In other words, orienting the pair of flexible arms 402 relative to two pieces of tissue includes moving cables 432 of each flexible arm of the pair of flexible arms 402 using a plurality of motors 418.

While the suturing device 400 shown in FIG. 4A illustrates flexible arms with hollow tubes 414 having cables 432 on the outside of the hollow tube 414 and the cables 432 passing through aligning blocks 440, in some embodiments, the cable 432 is integrated into a sidewall of the flexible tube. In this way, each hollow tube includes cables 432 within the sidewall of the flexible tube that can freely slide to facilitate the actuation and flexing of the flexible arm. In either embodiment, the cables 432 are movable along a longitudinal axis of the hollow tube and movable with respect to the sidewall of the hollow tube.

Referring back to FIG. 4A, and as noted above, each flexible arm 402a, 402b of the pair of flexible arms 402 includes a hollow tube 414. The hollow tube 414 allows the aforementioned flexibility and allows a suction force to be applied the tissue. For example, a pump 448 is mechanically attached to the hollow tube 414 and pumps air out of the hollow tube 414 to generate the suction force through the hollow tube 414. In some examples, the pump 448 is a vacuum pump.

When the surgeon presses the button 429 of the input device 424, the pumps 448 turn on, and when the surgeon releases the button 429, the pumps 448 turn off. In this way, the control electronics 422, by the command of the input device 424, cause the suturing device 400 to pump air to cause a suction between the tissue and each flexible arm of the pair of flexible arms 402. As noted above, this suction capability can force the tissue to engage with the flexible arms 402 to allow better manipulation of the tissue compared to a suturing device without a suction capability. In this way, the pumps 448 generate a suction force through the pair of flexible arms to draw the tissue towards the pair of flexible arms. For example, the suction can be used to draw the two pieces of tissue toward the corresponding flexible arm, and the flexible arms can be moved together to form a protrusion.

Referring to FIG. 4B, the flexible arms 402 engage two pieces of tissue 454a, 454b (generally 454), force the two pieces of tissue 454 together, and form a protrusion 456. Once the protrusion 456 is formed, the surgeon manipulates the joystick 428 which causes the processor to send a control signal to the actuator 416 to actuate the third flexible arm 404. In this way, the processor of the control electronics 422 is configured to control movement of third flexible arm 404.

The third flexible arm 404 includes a hollow tube 458. In some embodiments, the hollow tube 458 is substantially similar to, or the same as, the hollow tube 414 of the pair of flexible arms 402. However, the hollow tube 458 passes the sterile thread 410 between the thread supply 412 and the movable needle 408 instead of being used for a suction capability. The hollow tube 458 also passes communication cables between the control electronics 422 and a needle motor 460 operable to rotate the movable needle 408.

In this way, when the surgeon presses button 430, the movable needle 408 rotationally advances and threads the sterile thread 410 through both pieces of tissue defining the protrusion 456. In this way, the processor of the control electronics 422 is configured to control an angular position of the movable needle 408 with respect to the third flexible arm 404.

Figure 4C:
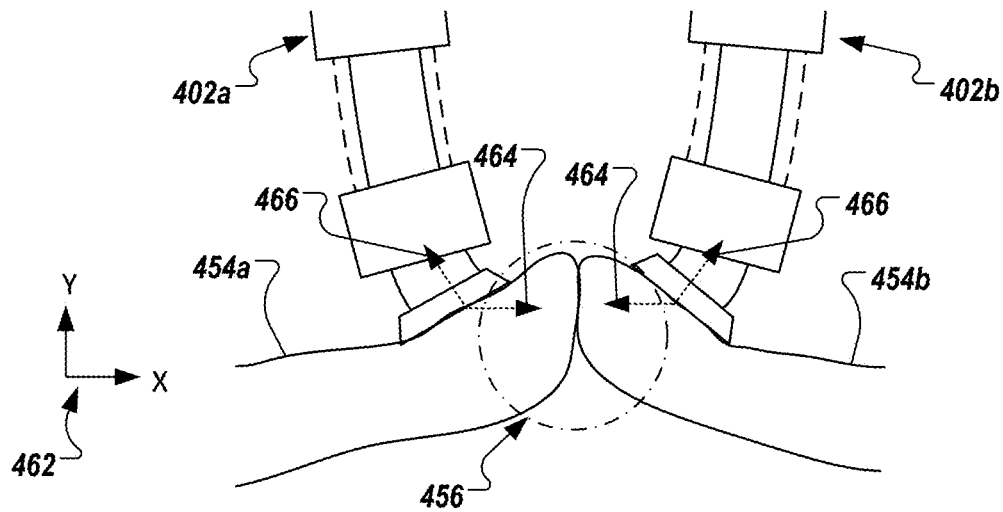

FIG. 4C illustrates the forces applied to the tissue 454 by the flexible arms 402. Each of the flexible arms 402 cause the tissue 454 to be forced in a direction along the longitudinal axis of the flexible arms 402 (e.g., force 466) because of the suction force. Also, referring to the coordinate system 462, each of the flexible arms 402 apply a force 464 toward each other along the x-direction. As a result, the two pieces of tissue 454 are forced together to form the protrusion 456.

Figure 4D:
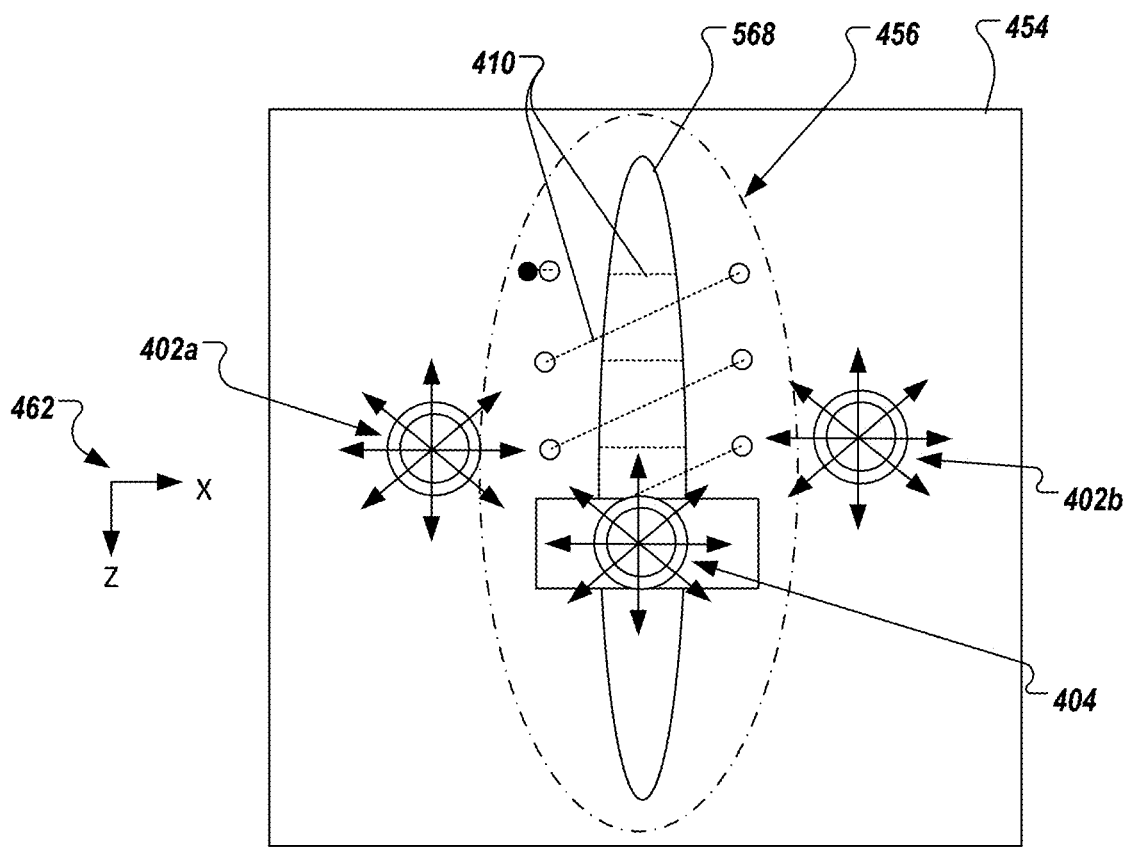

FIG. 4D is a top view of the protrusion 456 showing a suture in progress. In this example, an incision 568 exists in the tissue 454 of an anatomical organ. To apply the suture, the suture device 400 first applies a suture towards the top of the figure (e.g., as viewed in the plane of FIG. 4D) and the suture device 400 moves incrementally downward to create multiple sutures along the incision 568. The incision 568 is shown as a wide opening to emphasize the sterile thread 410 underneath the tissue 454. For example, the joystick 428 causes the processor to cause the third flexible arm 404 to move along the protrusion 456 and apply a suture at a plurality of locations along the protrusion 456 and/or the incision 568.

FIG. 4D also illustrates the movement degree of freedom for each of the flexible arms 402, 404. For example, while the above description generally referenced movement within a single plane, the actuators 416 allow for movement orthogonal to the plane as well. As a result, the distal end of each of the flexible arms 402, 404 is controllable in two orthogonal axes to give at least two positional degrees of freedom to each of the each of the flexible arms 402, 404. For example, referring to coordinate system 462, each of the flexible arms 402, 404 can be controlled to move in the x- and z-directions by the action of the actuator 416. For example, in some embodiments, this is implemented by using motors 418 and cables 432 in an orthogonal plane to the plane shown in FIG. 4A. Motion in the y-direction occurs as a result of the motion in the x and z directions, e.g., because of the pendulum-like motion of each of the flexible arms 402, 404.

FIGS. 5A-5E shows an experimental suturing device 500. Many aspects of the suturing device 500 are substantially similar to, or the same as, the suturing device 400. For example, the suturing device 500 includes an input device 502, control electronics 504, an actuator 506 with stepper motors 508 and winding modules 510, cables 512, an end cap 514, and a pair of flexible arms 516.

Figure 5A:
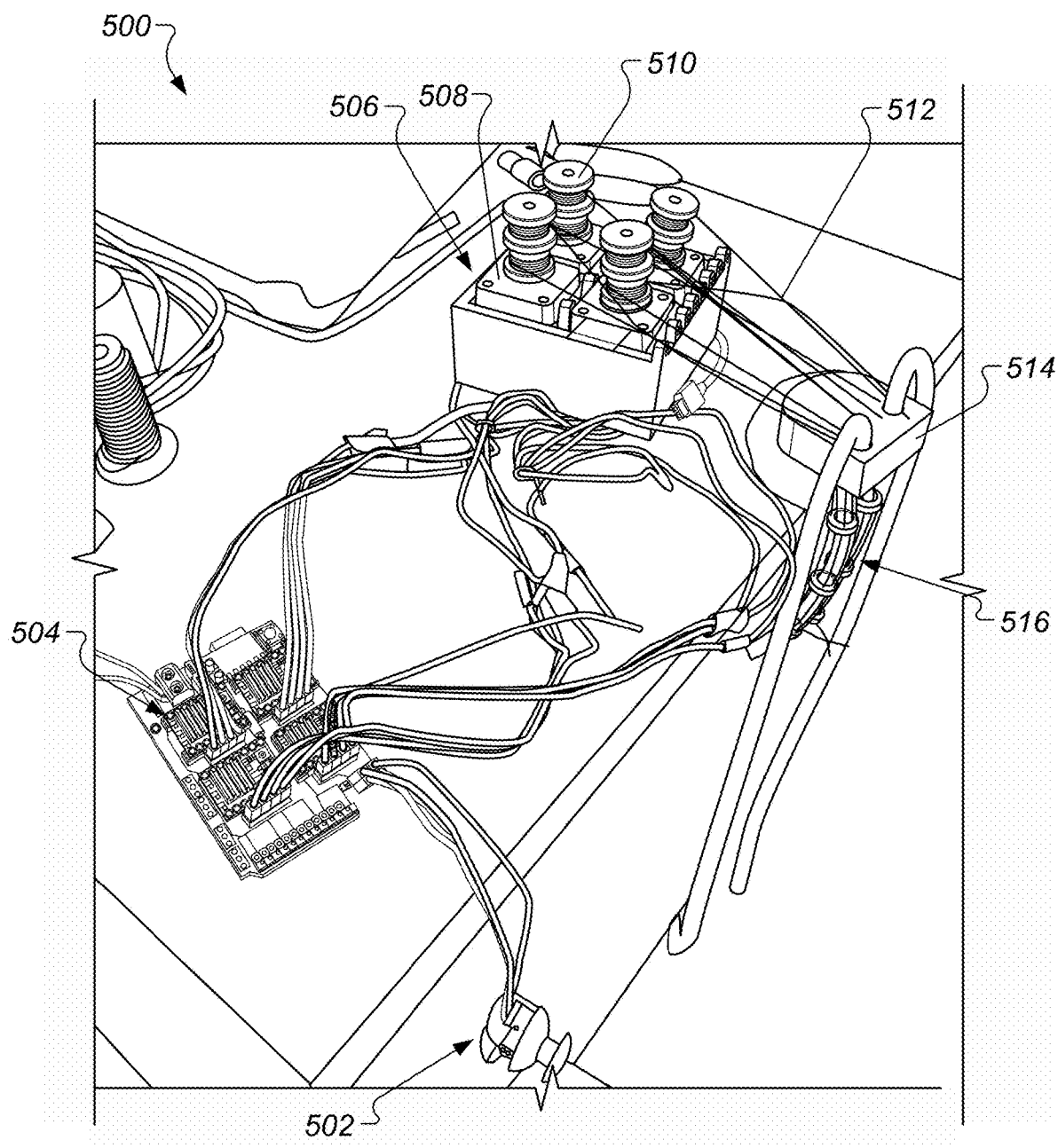
Figure 5B:
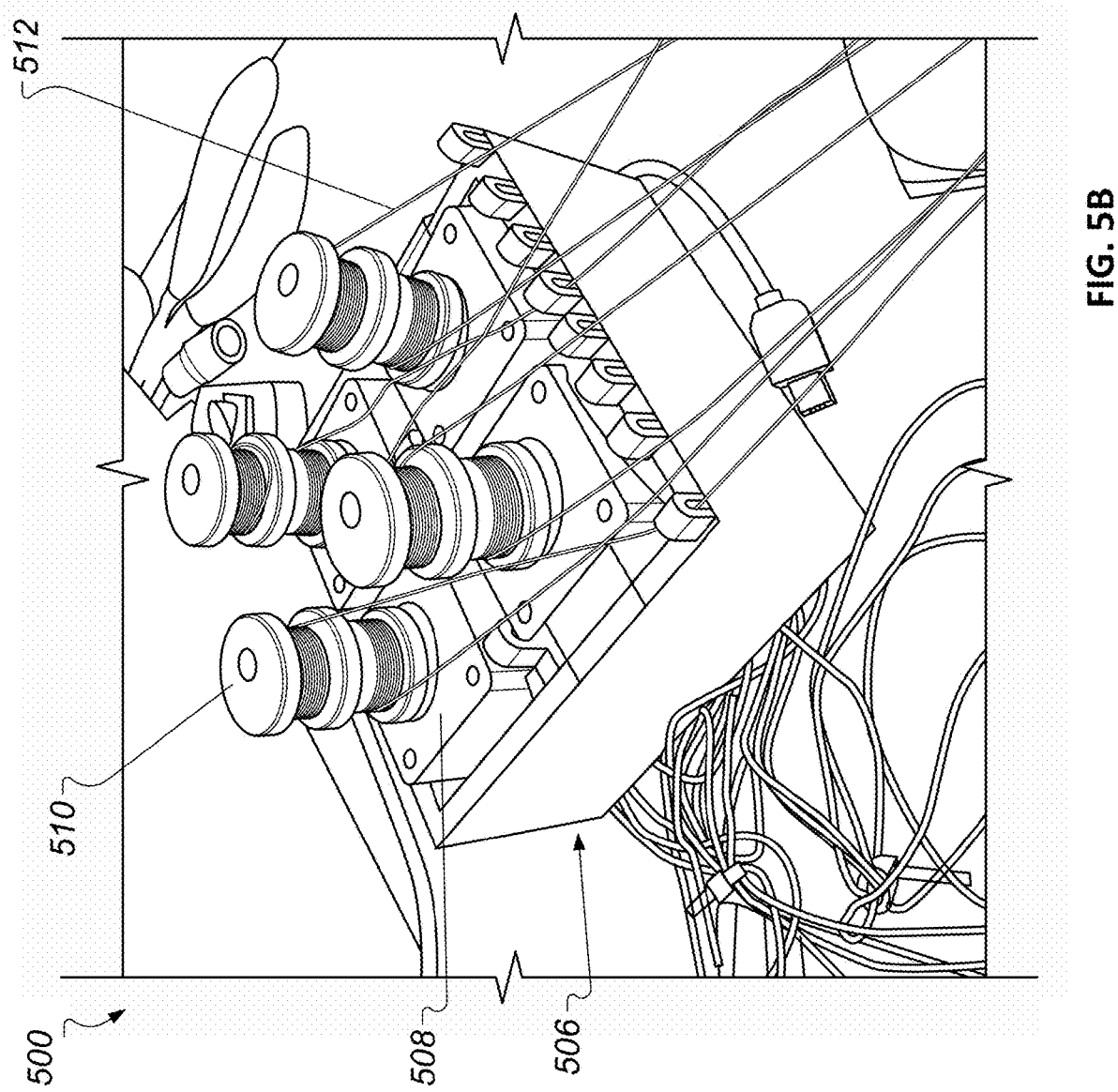

FIG. 5B shows a close-up view of the actuator 506 with four NEMA-14 stepper motors 508 and winding modules 510. The winding modules include two oppositely-wound spools of cables. Each spool is separated along the direction of rotation of the winding module 510.

FIG. 5C shows a close-up view of the pair of flexible arms 516a, 516b. Each flexible arm 516 including a hollow tube 518, two aligning blocks 520, and an end block 522. Each flexible arm 516 includes four cables 512 that are slidably received through the end cap 514, each aligning block 520 and terminate at the end block 522. The four cables 512 for each flexible arm 516 allow each arm to move in at least two degrees of freedom as described above with reference to FIG. 4D. In this example, a syringe (e.g., a 16 mL syringe) (not explicitly shown) is used instead of a pump to generate suction within the hollow tubes 518.

Figure 5D:
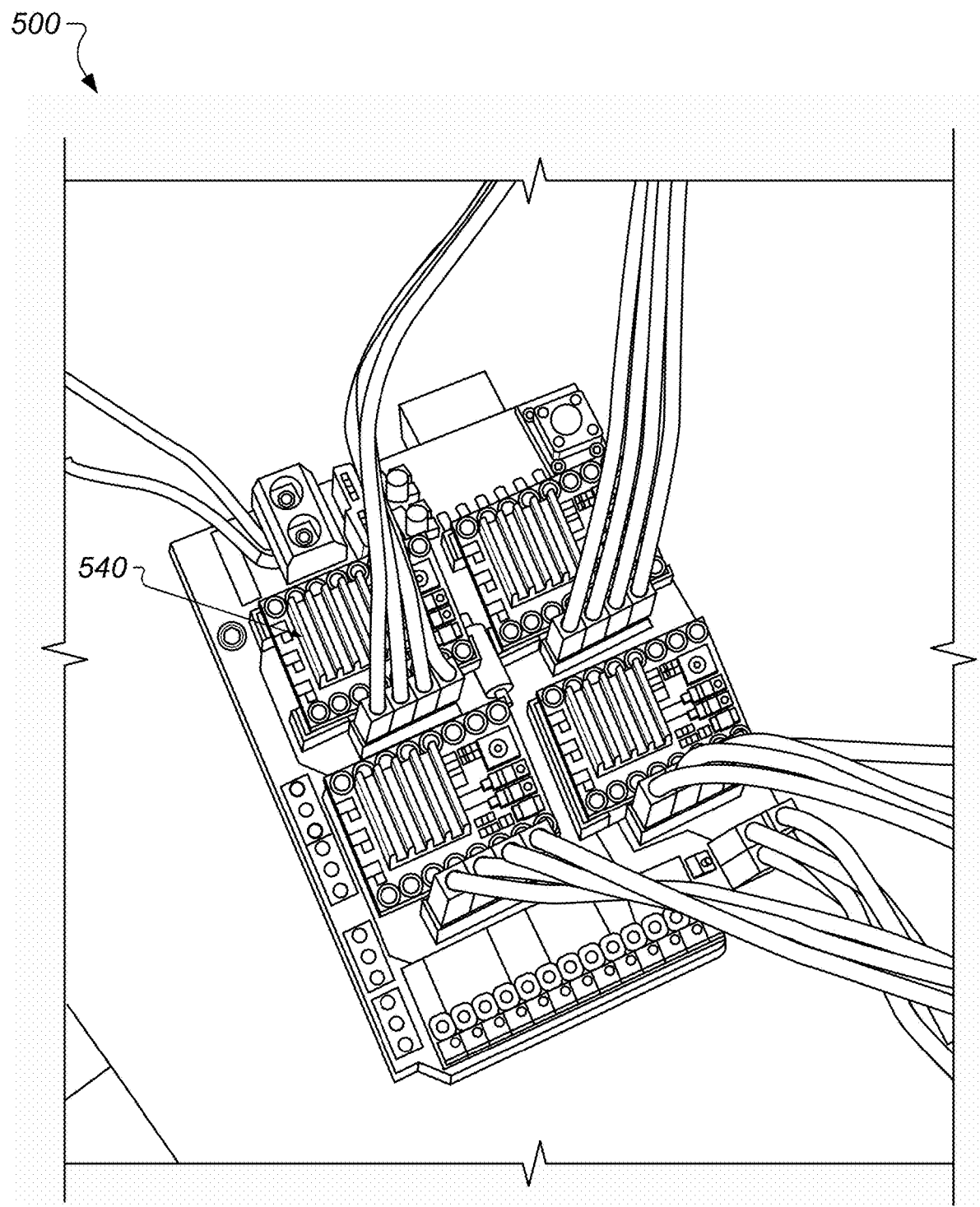

FIG. 5D is a close-up of the control electronics 504 for the suturing device 500. In some examples, the control electronics 504 includes some or all of the computational hardware described with reference to FIG. 7 below. The control electronics 504 includes stepper motor controllers 540 to control the actuators of the suturing device 500. Software of the control electronics 504 is implemented using an Arduino shield protocol. The processors of the control electronics 504 execute the software to process the input commands from the input device 502 (shown in FIG. 5A) and generate control signals to the actuators 506. The control electronics 504 is in electric communication with a power source and a voltage regulator to provide power to the control electronics 504 and the actuators 506.

Figure 5E:
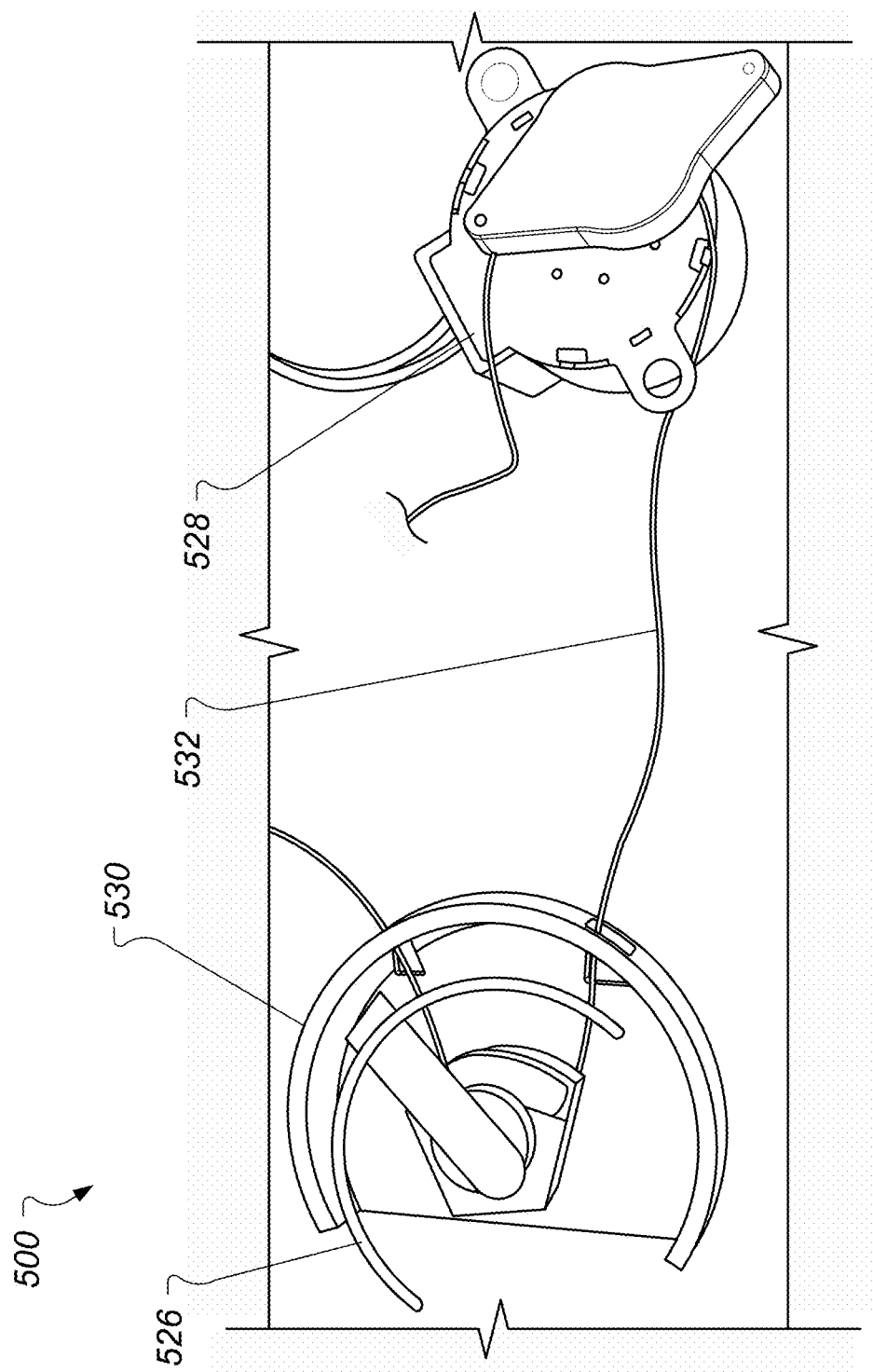

FIG. 5E is a close-up of a movable needle 526 for applying a suture. The movable needle 526 is a semi-circular needle and an angular position of the movable needle 526 is controlled using a needle motor 528. The movable needle 526 is rotatable about an axis of the housing 530 so that the needle can move between a position where the needle tip is exposed from the housing 530 (e.g., as shown in FIG. 5E) and a position where the needle tip is concealed within the housing 530 (not explicitly shown). The housing 530 is mountable to a third flexible arm that can be manipulated to apply the suture using the movable needle 526. For example, the housing 530 can be bolted or bonded to the third flexible arm.

The needle motor 528 is also in communication with the control electronics 504. The needle motor 528 is mechanically detached from the housing 530 and the angular position of the needle motor 528 is communicated to the movable needle 526 using cables 532. In this way, when the needle motor 528 rotates the movable needle 526 also rotates. Sterile thread is also attached to the moveable needle 526 for applying the suture (not explicitly shown in FIG. 5E).

Figure 6:
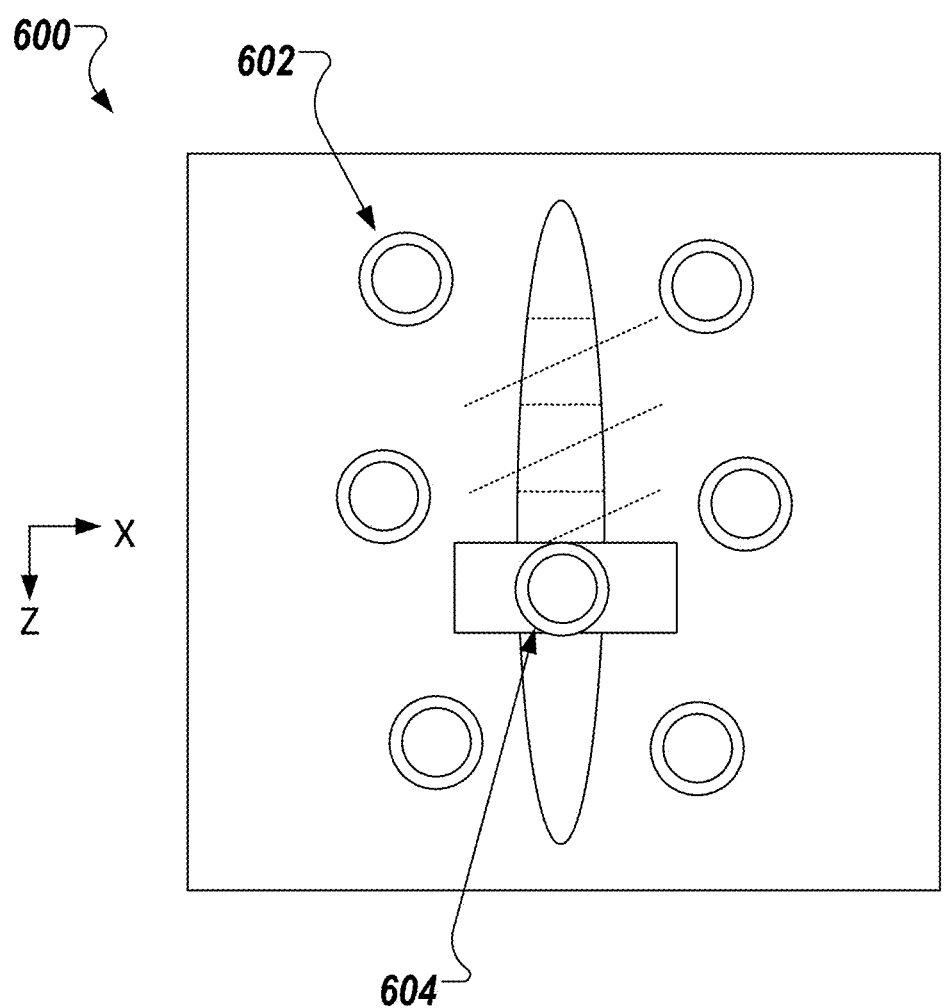
FIG. 6 is a schematic of a suturing device with seven flexible arms and an example use of the suturing device to apply a suture to two pieces of tissue.

While the above-described suturing devices 200, 400, 500 include a single pair of flexible arms, some suturing devices can include more than one pair of flexible arms. For example, FIG. 6 shows a schematic of a suturing device with three pairs of flexible arms 602 and a seventh flexible arm 604 for applying a suture.

Figure 7:
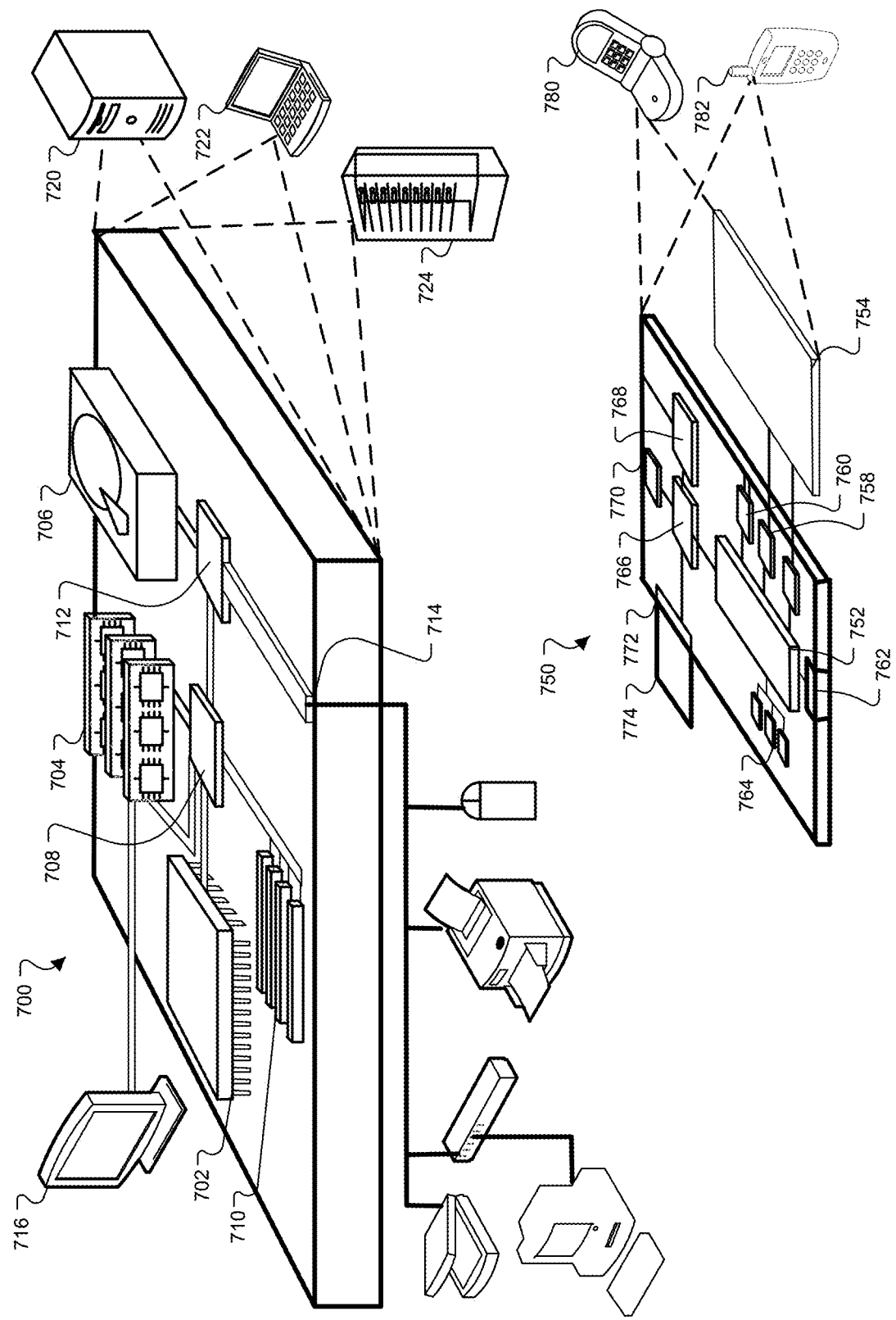
FIG. 7 is a block diagram of computer systems forming part of a suturing device.

FIG. 7 is a diagram of computer systems forming part of the suturing device according to some embodiments. For example, a computing device 700 and example mobile computing device 750 which can be used to implement the techniques previously described. Computing device 700 is intended to represent various forms of digital computers, including, e.g., laptops, desktops, workstations, personal digital assistants, servers, blade servers, mainframes, and other appropriate computers. Computing device 750 is intended to represent various forms of mobile devices, including, e.g., personal digital assistants, tablet computing devices, cellular telephones, smartphones, and other similar computing devices. The components shown here, their connections and relationships, and their functions, are meant to be examples only, and are not meant to limit implementations of the techniques described and/or claimed in this document.

Computing device 700 includes processor 702, memory 704, storage device 706, high-speed interface 708 connecting to memory 704 and high-speed expansion ports 710, and low speed interface 720 connecting to low speed bus 714 and storage device 706. Each of components 702, 704, 706, 708, 710, and 720, are interconnected using various busses, and can be mounted on a common motherboard or in other manners as appropriate. Processor 702 can process instructions for execution within computing device 700, including instructions stored in memory 704 or on storage device 706 to display graphical data for a GUI on an external input/output device, including, e.g., display 716 coupled to high speed interface 708. In other implementations, multiple processors and/or multiple busses can be used, as appropriate, along with multiple memories and types of memory. Also, multiple computing devices 700 can be connected, with each device providing portions of the necessary operations (e.g., as a server bank, a group of blade servers, or a multi-processor system).

Memory 704 stores data within computing device 700. In one implementation, memory 704 is a volatile memory unit or units. In another implementation, memory 704 is a non-volatile memory unit or units. Memory 704 also can be another form of computer-readable medium (e.g., a magnetic or optical disk. Memory 704 may be non-transitory.)

Storage device 706 is capable of providing mass storage for computing device 700. In one implementation, storage device 706 can be or contain a computer-readable medium (e.g., a floppy disk device, a hard disk device, an optical disk device, or a tape device, a flash memory or other similar solid state memory device, or an array of devices, such as devices in a storage area network or other configurations.) A computer program product can be tangibly embodied in a data carrier. The computer program product also can contain instructions that, when executed, perform one or more methods (e.g., those described above.) The data carrier is a computer- or machine-readable medium, (e.g., memory 704, storage device 706, memory on processor 702, and the like.)

High-speed controller 708 manages bandwidth-intensive operations for computing device 700, while low speed controller 720 manages lower bandwidth-intensive operations. Such allocation of functions is an example only. In one implementation, high-speed controller 708 is coupled to memory 704, display 716 (e.g., through a graphics processor or accelerator), and to high-speed expansion ports 710, which can accept various expansion cards (not shown). In the implementation, low-speed controller 720 is coupled to storage device 706 and low-speed expansion port 714. The low-speed expansion port, which can include various communication ports (e.g., USB, Bluetooth®, Ethernet, wireless Ethernet), can be coupled to one or more input/output devices, (e.g., a keyboard, a pointing device, a scanner, or a networking device including a switch or router, e.g., through a network adapter.)

Computing device 700 can be implemented in a number of different forms, as shown in the FIG. 7. For example, it can be implemented as standard server 720, or multiple times in a group of such servers. It also can be implemented as part of rack server system 724. In addition or as an alternative, it can be implemented in a personal computer (e.g., laptop computer 722.) In some examples, components from computing device 700 can be combined with other components in a mobile device (not shown), e.g., device 750. Each of such devices can contain one or more of computing device 700, 750, and an entire system can be made up of multiple computing devices 700, 750 communicating with each other.

Computing device 750 includes processor 752, memory 764, an input/output device (e.g., display 754, communication interface 766, and transceiver 768) among other components. Device 750 also can be provided with a storage device, (e.g., a microdrive or other device) to provide additional storage. Each of components 750, 752, 764, 754, 766, and 768, are interconnected using various buses, and several of the components can be mounted on a common motherboard or in other manners as appropriate.

Processor 752 can execute instructions within computing device 750, including instructions stored in memory 764. The processor can be implemented as a chipset of chips that include separate and multiple analog and digital processors. The processor can provide, for example, for coordination of the other components of device 750, e.g., control of user interfaces, applications run by device 750, and wireless communication by device 750.

Processor 752 can communicate with a user through control interface 758 and display interface 756 coupled to display 754. Display 754 can be, for example, a TFT LCD (Thin-Film-Transistor Liquid Crystal Display) or an OLED (Organic Light Emitting Diode) display, or other appropriate display technology. Display interface 756 can comprise appropriate circuitry for driving display 754 to present graphical and other data to a user. Control interface 758 can receive commands from a user and convert them for submission to processor 752. In addition, external interface 762 can communicate with processor 742, so as to enable near area communication of device 750 with other devices. External interface 762 can provide, for example, for wired communication in some implementations, or for wireless communication in other implementations, and multiple interfaces also can be used.

Memory 764 stores data within computing device 750. Memory 764 can be implemented as one or more of a computer-readable medium or media, a volatile memory unit or units, or a non-volatile memory unit or units. Expansion memory 774 also can be provided and connected to device 750 through expansion interface 772, which can include, for example, a SIMM (Single In Line Memory Module) card interface. Such expansion memory 774 can provide extra storage space for device 750, or also can store applications or other data for device 750. Specifically, expansion memory 774 can include instructions to carry out or supplement the processes described above, and can include secure data also. Thus, for example, expansion memory 774 can be provided as a security module for device 750, and can be programmed with instructions that permit secure use of device 750. In addition, secure applications can be provided through the SIMM cards, along with additional data, (e.g., placing identifying data on the SIMM card in a non-hackable manner.)

The memory can include, for example, flash memory and/or NVRAM memory, as discussed below. In one implementation, a computer program product is tangibly embodied in a data carrier. The computer program product contains instructions that, when executed, perform one or more methods, e.g., those described above. The data carrier is a computer- or machine-readable medium (e.g., memory 764, expansion memory 774, and/or memory on processor 752), which can be received, for example, over transceiver 768 or external interface 762.

Device 750 can communicate wirelessly through communication interface 766, which can include digital signal processing circuitry where necessary. Communication interface 766 can provide for communications under various modes or protocols (e.g., GSM voice calls, SMS, EMS, or MMS messaging, CDMA, TDMA, PDC, WCDMA, CDMA1500, or GPRS, among others.) Such communication can occur, for example, through radio-frequency transceiver 768. In addition, short-range communication can occur, e.g., using a Bluetooth®, WiFi, or other such transceiver (not shown). In addition, GPS (Global Positioning System) receiver module 770 can provide additional navigation- and location-related wireless data to device 750, which can be used as appropriate by applications running on device 750. Sensors and modules such as cameras, microphones, compasses, accelerators (for orientation sensing), etc. may be included in the device.

Device 750 also can communicate audibly using audio codec 760, which can receive spoken data from a user and convert it to usable digital data. Audio codec 760 can likewise generate audible sound for a user, (e.g., through a speaker in a handset of device 750.) Such sound can include sound from voice telephone calls, can include recorded sound (e.g., voice messages, music files, and the like) and also can include sound generated by applications operating on device 750.

Computing device 750 can be implemented in a number of different forms, as shown in the FIG. 7. For example, it can be implemented as cellular telephone 780. It also can be implemented as part of smartphone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor. The programmable processor can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to a computer program product, apparatus and/or device (e.g., magnetic discs, optical disks, memory, Programmable Logic Devices (PLDs)) used to provide machine instructions and/or data to a programmable processor, including a machine-readable medium that receives machine instructions.

To provide for interaction with a user, the systems and techniques described here can be implemented on a computer having a device for displaying data to the user (e.g., a CRT (cathode ray tube) or LCD (liquid crystal display) monitor), and a keyboard and a pointing device (e.g., a mouse or a trackball) by which the user can provide input to the computer. Other kinds of devices can be used to provide for interaction with a user as well; for example, feedback provided to the user can be a form of sensory feedback (e.g., visual feedback, auditory feedback, or tactile feedback); and input from the user can be received in a form, including acoustic, speech, or tactile input.

The systems and techniques described here can be implemented in a computing system that includes a backend component (e.g., as a data server), or that includes a middleware component (e.g., an application server), or that includes a frontend component (e.g., a client computer having a user interface or a Web browser through which a user can interact with an implementation of the systems and techniques described here), or a combination of such back end, middleware, or frontend components. The components of the system can be interconnected by a form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A suturing device comprising:
   a pair of flexible arms configured to force two pieces of tissue together and form a protrusion defined by the two pieces of tissue;
   a third flexible arm comprising a movable needle configured to apply a suture through both pieces of tissue defining the protrusion;
   an actuator configured to move each flexible arm of the pair of flexible arms independently relative to the tissue and move the third flexible arm relative to the tissue; and
   a pump configured to generate a suction force through the pair of flexible arms to draw the tissue towards the pair of flexible arms.

2. The suturing device of claim 1, wherein each flexible arm of the pair of flexible arms comprises a hollow tube configured to engage the tissue.

3. The suturing device of claim 2, wherein the pump is configured to generate the suction force through each hollow tube.

4. The suturing device of claim 2, wherein each hollow tube comprises cables within a sidewall of the hollow tube.

5. The suturing device of claim 4, wherein the cables are movable along a longitudinal axis of the hollow tube and movable with respect to the sidewall of the hollow tube.

6. The suturing device of claim 1, wherein the actuator comprises a plurality of motors with winding modules.

7. The suturing device of claim 1, further comprising a needle motor configured to cause the movable needle to rotate about an axis perpendicular to a longitudinal axis of the third flexible arm.

8. The suturing device of claim 1, wherein the movable needle is a semi-circular needle movable relative to the third flexible arm.

9. The suturing device of claim 1, wherein the tissue is a tissue of an anatomical organ.

10. The suturing device of claim 1, wherein the pump is a vacuum pump.

11. The suturing device of claim 1, wherein the actuator comprises a plurality of stepper motors.

12. The suturing device of claim 1, wherein at least a portion of the pair of flexible arms and the at least a portion of the third flexible arm are configured to be disposed inside an endoscope.

13. The suturing device of claim 1, further comprising a processor configured to control movement of the pair of flexible arms, the third flexible arm, and an angular position of the movable needle with respect to the third flexible arm.

14. The suturing device of claim 13, wherein the processor is controllable by an input device.

15. The suturing device of claim 1, wherein a distal end of each flexible arm comprises a flange that engages the tissue.

\* \* \* \* \*